(12) United States Patent
Inoue et al.

(10) Patent No.: US 9,847,210 B2
(45) Date of Patent: Dec. 19, 2017

(54) PARTICLE BEAM IRRADIATION APPARATUS FOR IRRADIATING A SUBJECT WITH AN ARBITRARY NUMBER OF PARTICLES

(71) Applicant: Mitsubishi Electric Corporation, Chiyoda-ku (JP)

(72) Inventors: Hiroshi Inoue, Chiyoda-ku (JP); Yusuke Sakamoto, Chiyoda-ku (JP); Kazuo Yamamoto, Chiyoda-ku (JP)

(73) Assignee: Mitsubishi Electric Corporation, Chiyoda-ku (JP)

( * ) Notice: Subject to any disclaimer, the term of this patent is extended or adjusted under 35 U.S.C. 154(b) by 0 days.

(21) Appl. No.: 15/285,567

(22) Filed: Oct. 5, 2016

(65) Prior Publication Data
US 2017/0133200 A1    May 11, 2017

(30) Foreign Application Priority Data

Nov. 11, 2015 (JP) .................... 2015-221251
Jul. 25, 2016 (JP) .................... 2016-145091

(51) Int. Cl.
*A61N 5/10* (2006.01)
*G21K 5/04* (2006.01)
(Continued)

(52) U.S. Cl.
CPC .......... *H01J 37/304* (2013.01); *A61N 5/1048* (2013.01); *A61N 5/1077* (2013.01); *H01J 37/244* (2013.01); *H01J 37/3023* (2013.01)

(58) Field of Classification Search
CPC .. A61N 5/1067; A61N 5/1049; A61N 5/1042; A61N 5/1048; A61N 5/1064; A61N 5/1077; A61N 5/10; A61N 5/1043; A61N 5/1081; A61N 5/107; A61N 5/1082; A61N 5/01; A61N 5/1037; A61N 5/1079;
(Continued)

(56) References Cited

U.S. PATENT DOCUMENTS 4,992,746 A * 2/1991 Martin ............... H05H 9/00
                                              313/555
5,668,371 A * 9/1997 Deasy ............... A61N 5/1042
                                              250/505.1
(Continued)

FOREIGN PATENT DOCUMENTS

JP        11-233300        8/1999

*Primary Examiner* — David A Vanore
(74) *Attorney, Agent, or Firm* — Oblon, McClelland, Maier & Neustadt, L.L.P.

(57) ABSTRACT

A particle beam irradiation apparatus includes an accelerator that extracts a pulse-shaped particle beam and a switching system that switches a particle beam to prevent irradiation of a subject. The apparatus also includes a database in which a time dependency of the number of particles in one pulse of the particle beam is stored in association with a driving condition of the accelerator. A computer processor calculates a timing of switching by the switching system, based on a desired accumulated number of particles to be irradiated onto the irradiation subject and the time dependency of the number of particles in one pulse of the particle beam, and a switching controller controls the switching system based on the timing of switching calculated by the computer processor.

7 Claims, 7 Drawing Sheets

(51) Int. Cl.
*H01J 37/304* (2006.01)
*H01J 37/244* (2006.01)
*H01J 37/302* (2006.01)

(58) Field of Classification Search
CPC .. A61N 5/1044; A61N 5/1068; A61N 5/1071; A61N 5/1075; A61N 5/1084; G21K 1/093; G21K 1/046; G21K 1/04; G21K 1/08; G21K 1/087; G21K 1/10; G21K 5/04; G21K 5/10; G21K 5/02; H05H 13/04; H05H 7/00; H05H 7/10; H05H 7/08; H05H 9/00; A61B 5/64; A61B 5/007; A61B 5/02028; A61B 5/066; A61B 5/1128; A61B 5/7285; A61B 5/7292; A61B 5/741; A61B 5/743
USPC ............ 378/65, 95, 150, 34, 68, 69, 8; 250/396 R, 492.1, 505.1, 395, 360.1, 389, 250/393, 396 ML, 398, 400, 454.11, 250/503.1; 315/507, 501, 503, 502; 600/1, 407, 428
See application file for complete search history.

(56) References Cited

U.S. PATENT DOCUMENTS

| | | | |
|---|---|---|---|
| 5,724,400 A * | 3/1998 | Swerdloff | A61B 6/00 378/150 |
| 5,751,781 A * | 5/1998 | Brown | A61N 5/1042 378/65 |
| 5,969,367 A * | 10/1999 | Hiramoto | A61N 5/1042 250/492.3 |
| 6,472,834 B2 * | 10/2002 | Hiramoto | G21K 5/04 250/396 R |
| 6,621,889 B1 * | 9/2003 | Mostafavi | A61B 6/541 378/65 |
| 6,717,162 B1 * | 4/2004 | Jongen | A61N 5/1042 250/492.1 |
| 6,937,696 B1 * | 8/2005 | Mostafavi | A61B 5/7292 378/65 |
| 9,044,600 B2 * | 6/2015 | Balakin | A61N 5/10 |
| 9,168,392 B1 * | 10/2015 | Balakin | A61N 5/1049 |
| 9,314,649 B2 * | 4/2016 | Balakin | A61N 5/107 |
| 2004/0116804 A1 * | 6/2004 | Mostafavi | A61B 5/113 600/428 |
| 2004/0162457 A1 * | 8/2004 | Maggiore | A61N 5/10 600/1 |
| 2007/0170994 A1 * | 7/2007 | Peggs | H05H 13/04 331/34 |
| 2008/0023644 A1 * | 1/2008 | Pedroni | A61N 5/10 250/400 |
| 2008/0067451 A1 * | 3/2008 | Guertin | A61N 5/10 250/503.1 |
| 2009/0309046 A1 * | 12/2009 | Balakin | A61N 5/1049 250/492.3 |
| 2010/0059687 A1 * | 3/2010 | Balakin | A61N 5/1048 250/396 R |
| 2011/0249088 A1 * | 10/2011 | Hannibal | A61N 5/1048 348/43 |
| 2011/0313232 A1 * | 12/2011 | Balakin | A61N 5/10 600/1 |
| 2012/0241635 A1 * | 9/2012 | Luechtenborg | A61N 5/1043 250/389 |
| 2013/0092839 A1 * | 4/2013 | Kraft | A61N 5/1043 250/360.1 |
| 2015/0374324 A1 * | 12/2015 | Nishimura | A61N 5/1071 600/1 |
| 2016/0136461 A1 * | 5/2016 | Iwata | A61N 5/1079 600/1 |
| 2016/0317836 A1 * | 11/2016 | Lee | A61N 5/1077 |

* cited by examiner

PARTICLE BEAM IRRADIATION APPARATUS FOR IRRADIATING A SUBJECT WITH AN ARBITRARY NUMBER OF PARTICLES

BACKGROUND OF THE INVENTION

Field of the Invention

The present invention relates to a particle beam irradiation apparatus that is utilized in particle beam therapy for treating a focus such as a tumor.

Description of the Related Art

A particle beam irradiation apparatus is an apparatus that irradiates beam-shaped particles such as hydrogen ions or carbon ions, accelerated by an accelerator, onto a subject. When a particle beam is irradiated onto a focus such as a tumor, a high-accuracy control of the number of irradiation particles is required for the purpose of securely removing the focus and preventing a healthy organ therebehind from being injured.

In a conventional particle beam irradiation apparatus, a beam control parameter such as the acceleration frequency of an accelerator for extracting a pulse-shaped particle beam is controlled so that the number of particles per pulse is controlled, and the number of pulses to be irradiated is controlled by use of a beam shutter (e.g., refer to Patent Document 1).

PRIOR ART REFERENCE

Patent Document

[Patent Document 1]
Japanese Patent Application Laid-Open No. H11-233300 (Pages 3 and 4, FIG. 1)

However, in the conventional method of controlling the beam control parameter of the accelerator so as to control the number of particles per pulse, the number of particles per pulse is set based on a table in which a predetermined discrete beam control parameter and the number of particles per pulse are matched to each other. Accordingly, the accumulated number of particles in a particle beam to be irradiated is limited to the number of particles per pulse or a multiple thereof; thus, it is difficult to set the number of accumulated particle beams to an arbitrary value.

The present invention has been implemented in order to solve the foregoing problem; the objective thereof is to obtain a particle beam irradiation apparatus that makes it possible to set the accumulated number of particles in a particle beam to be irradiated to an arbitrary value.

SUMMARY OF THE INVENTION

A particle beam irradiation apparatus according to the present invention includes an accelerator that extracts a particle beam of a pulse shape, a switching system that has a function of switching the particle beam of a pulse shape extracted from the accelerator in order not to be irradiated onto an irradiation subject, a database in which time dependency of the number of particles in one pulse of the particle beam is stored in accordance with a driving condition for the accelerator, a computing processing unit that calculates a timing of switching operation by the switching system, based on a desired accumulated number of particles to be irradiated onto the irradiation subject and the time dependency of the number of particles in one pulse of the particle beam, that is stored in the database, and a switching controller that controls the switching system, based on the timing of switching operation by the switching system, that is calculated by the computing processing unit.

The present invention includes a database in which time dependency of the number of particles in one pulse of the particle beam is stored in accordance with a driving condition for the accelerator and a computing system that calculates a timing of switching operation by the switching system, based on a desired accumulated number of particles to be irradiated onto the irradiation subject and time dependency, of the number of particles in one pulse of the particle beam, that is stored in the database; therefore, the accumulated number of particles in a particle beam to be irradiated can be set to an arbitrary value.

The foregoing and other object, features, aspects, and advantages of the present invention will become more apparent from the following detailed description of the present invention when taken in conjunction with the accompanying drawings.

DETAILED DESCRIPTION OF THE PREFERRED EMBODIMENTS

Embodiment 1

Figure 1:
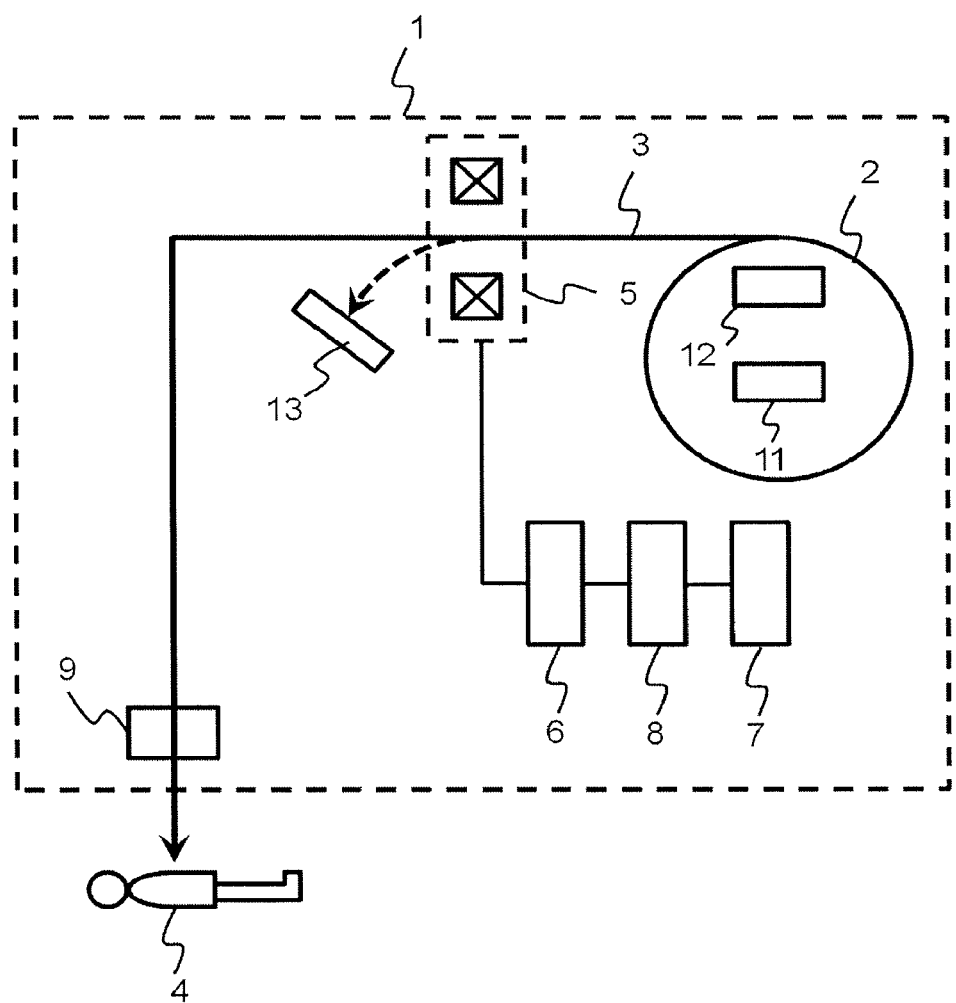
FIG. 1 is a schematic diagram of a particle beam irradiation apparatus representing Embodiment 1 of the present invention.

FIG. 1 is a schematic diagram of a particle beam irradiation apparatus according to Embodiment 1 for carrying out the present invention. As represented in FIG. 1, a particle beam irradiation apparatus 1 according to Embodiment 1 includes an accelerator 2, a kicker electromagnet 5, as a switching system, that is disposed on a beam line 3 of a pulse-shaped particle beam extracted from the accelerator 2 and has a function of switching the particle beam that is irradiated onto an irradiation subject 4, a kicker electromagnet controller 6, as a switching control system, that controls switching operation performed by the kicker electromagnet 5, a database 7 in which time dependency of the number of particles in one pulse of a particle beam is stored in accordance with a driving condition for the accelerator 2, and a computing processing unit 8, as a computing system, that calculates a timing of the switching operation by the kicker electromagnet 5, based on a desired accumulated number of particles to be irradiated onto an irradiation position (irradiation spot) in the irradiation subject 4 and the time dependency, of the number of particles in one pulse of a particle beam, that is stored in the database 7. The particle beam irradiation apparatus according to Embodiment 1 will be explained on the assumption that it is utilized in particle beam therapy for treating a focus such as a tumor. In this case, it is assumed that the irradiation subject 4 is the body of a human such as a patient; however, strictly speaking, the irradiation subject is a focus such as a tumor.

As the accelerator 2, for example, a synchrotron-type, synchrocyclotron-type, or fixed-field-strong-convergence-type circular accelerator can be utilized; the accelerator 2 is provided with an ion source 11 and an RF acceleration mechanism 12.

The ion source 11 is configured, for example, with a filament and an extraction electrode that is disposed in such a way as to face the filament. The space between the filament and the extraction electrode is filled, for example, with hydrogen gas or methane gas. When an electric current flows in the filament, thermoelectrons are emitted from the filament and then accelerated to move toward the extraction electrode; while moving to the extraction electrode, the thermoelectrons collide with the gas that has been filled into the space and then make the gas into plasma. In such a way as described above, the ion source 11 produces proton ions in the case where the filled gas is hydrogen or carbon ions in the case where the filled gas is methane gas. These proton ions or carbon ions will be referred to as particles, hereinafter. In Embodiment 1, the voltage to be applied between the filament and the extraction electrode is constant, and the amount of electric current that flows in the filament is controlled so that the number of particles is controlled.

For example, in the case of a cyclotron-type circular accelerator, the RF acceleration mechanism 12 is provided with a pair of D-shaped electrodes disposed at a position that is perpendicular to a magnetic field formed by an electromagnet. The cross section of each of the electrodes in the pair is semicircular; the respective straight portions of the semicircles are arranged in such a way as to face each other across a gap. The ion source 11 is disposed in the central portion of the pair of electrodes. A particle produced in the ion source 11 undergoes Lorenz force caused by the magnetic field formed by the electromagnet and hence makes circulating motion. The particle is accelerated by a voltage applied between the electrodes in the pair; while being accelerated, the radius of the circulation orbit of the particle increases gradually. In this situation, only a particle synchronized with an AC voltage to be applied between the electrodes in the pair is accelerated in the space between the electrodes in the pair; by periodically changing the frequency of the AC voltage, a particle having a frequency synchronized with the circulation orbit is accelerated. As a result, the accelerated particles form a beam-shaped and pulse-shaped particle beam. The energy of the beam can be controlled by controlling the AC voltage (acceleration voltage) to be applied between the electrodes in the pair. Therefore, the driving condition for the accelerator according to Embodiment 1 includes the amount of electric current that is made to flow in the filament and the acceleration voltage to be applied between the electrodes of the RF acceleration mechanism.

The kicker electromagnet 5, as a switching system, is configured with two electromagnets with which the beam line 3 is flanked, and has an air-core structure; the kicker electromagnet 5 has a function in which a magnetic field is applied at high speed to a particle beam transported on the beam line so that the particle beam is deflected so as to be diverted from the beam line 3. Speaking of the ability of the kicker electromagnet 5, for example, when it is assumed that the length of the air-core in the direction of the beam line 3 is 60 cm, a particle beam can be deflected by approximately 15° from the beam line 3 when the intensity of a magnetic field generated by the electromagnet is 1 T. In terms of contamination of the apparatus, it is required to absorb and extinguish a particle beam diverted from the beam line 3; thus, in Embodiment 1, the particle beam irradiation apparatus 1 is provided a beam damper 13 that absorbs and extinguishes a particle beam diverted from the beam line 3.

In the database 7, the amount of electric current that flows in the filament of the ion source 11 and the acceleration voltage to be applied between the electrodes of the RF acceleration mechanism 12 are utilized as parameters, and the time dependency of the number, of particles in one pulse of a particle beam, that corresponds to the parameters, is stored. As the time dependency of the number of particles in one pulse of a particle beam, the number of particles in each of division times (the number of particles per unit time) at a time when one pulse is temporally divided, the accumulated number of particles in one pulse at each of the division times, or the like is utilized.

The computing processing unit 8 receives from the database 7 data on the time dependency of the number of particles, related to a set amount of electric current that flows in the filament of the ion source 11 and a set acceleration voltage to be applied to the electrodes of the RF acceleration mechanism 12, and then calculates the irradiation time of a particle beam to be irradiated, in accordance with a desired accumulated number of particles, which is given from the outside, so as to compute the timing of the switching operation performed by the kicker electromagnet 5. The desired accumulated number of particles may not necessarily be given from the outside; it may be allowed that the desired accumulated number of particles is preliminarily stored in the database 7.

The kicker electromagnet controller 6 controls the switching operation performed by the kicker electromagnet 5 at the timing of the switching operation by the kicker electromagnet 5, which has been computed by the computing processing unit 8. Each of the kicker electromagnet controller 6 and the computing processing unit 8 is formed of a computer provided with a CPU and a memory; it may be allowed that the kicker electromagnet controller 6 and the computing processing unit 8 are formed of either a single computer or respective different computers.

Next, the time dependency of the number, of particles in one pulse of a particle beam, that corresponds to the driving condition, stored in the database 7, for the accelerator 2 will be explained. Before treatment with the particle beam irradiation apparatus is started, a particle number measurement monitor 9 is installed on the beam line 3 between the kicker electromagnet 5 and the irradiation subject 4. The particle number measurement monitor 9 can measure the number of particles passing through the beam line 3. As the particle number measurement monitor 9, an ionization chamber, for example, that does not hinder a particle beam from traveling on the beam line 3 can be utilized.

An ionization chanter is configured in such a way that two electrodes are arranged to face each other in a container filled with gas. When a particle beam passes through the space between the electrodes, the gas between the electrodes is ionized along the trajectory of the particle beam; as a result, the gas is separated into an ion having a positive electric charge and an electron having a negative charge. Because a voltage is applied across the two electrodes, the positive ion and the electron travel toward the negative electrode and the positive electrode, respectively; as a result, a short pulse current is produced. By measuring this electric current, the number of particles in the particle beam that has passed through the ionization chanter can be measured.

The amount of electric current that flows in the filament of the ion source 11 and the acceleration voltage applied across the electrodes of the RF acceleration mechanism 12 are set to various values that are assumed when the particle beam irradiation apparatus is utilized in a practical treatment; then, by utilizing these values as parameters, the time dependency of the number of particles in one pulse of a particle beam is measured on the beam line 3, by means of the particle number measurement monitor 9. In general, because the duration of one pulse is 0.1 to 5 µs, the particle number measurement monitor 9 measures the number of particles in a division time that is obtained by dividing the duration by 20 or so.

Figure 2:
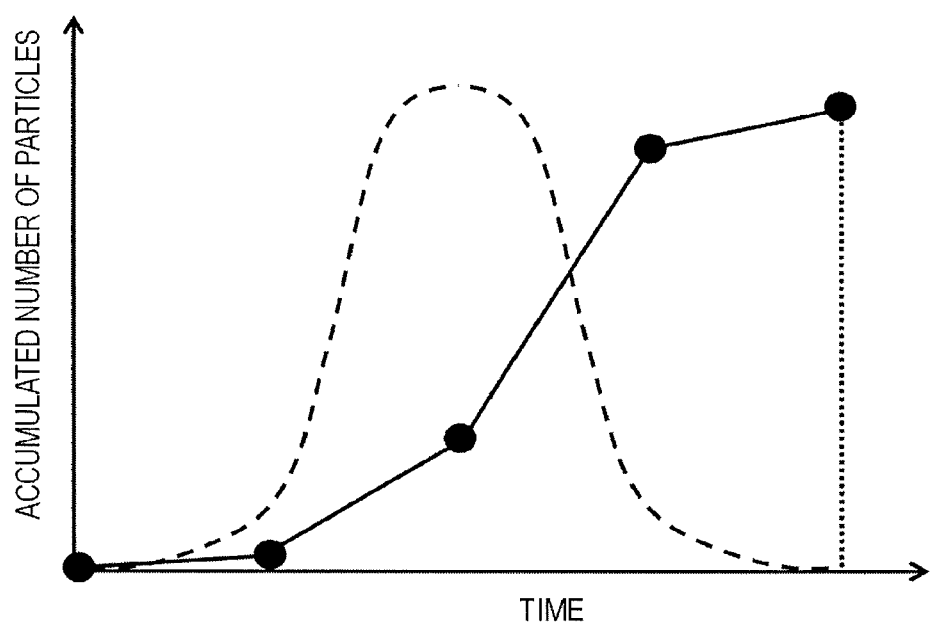
FIG. 2 is an explanatory graph for explaining time dependency of the number of particles in one pulse according to Embodiment 1 of the present invention.

FIG. 2 is an explanatory graph for explaining the time dependency, of the number of particles in one pulse, that is stored in the database 7. In FIG. 2, the abscissa and the ordinate denote the time and the accumulated number of particles, respectively. The broken line schematically represents a temporal particle distribution profile in one pulse. Through such a method as described above, the amount of electric current that flows in the filament of the ion source 11 and the acceleration voltage to be applied between the electrodes of the RF acceleration mechanism 12 are utilized as parameters, and the time dependency of the number, of particles in one pulse of a particle beam, that corresponds to the parameters, is stored in the database 7.

As described above, in accordance with a desired number of accumulated particles to be given from the outside, the computing processing unit 8 calculates the irradiation time of a particle beam to be irradiated and then computes the timing of the switching operation performed by the kicker electromagnet 5. Then, the kicker electromagnet controller 6 controls the switching operation performed by the kicker electromagnet 5 at the timing of the switching operation by the kicker electromagnet 5, which has been computed by the computing processing unit 8; however, a time difference occurs between the time point when the kicker electromagnet controller 6 receives the timing of the switching operation and the time point when the switching operation by the kicker electromagnet 5 is completed. In order to complete the switching operation by the kicker electromagnet 5 accurately in the irradiation time of a particle beam, which is computed by the computing processing unit 8, it is required to compensate this time difference. In order to compensate this time difference, the database 7 preliminarily stores the time difference between the time point when the kicker electromagnet controller 6 receives the timing of the switching operation from the computing processing unit 8 and the time point when the switching operation by the kicker electromagnet 5 is completed.

Next, the operation at a time when a practical treatment is carried out will be explained. In the explanation below, a case where a predetermined accumulated number of particles are irradiated by use of a single-pulse particle beam will be described.

Through a treatment plan or the like, a desired number of accumulated particles in a particle beam, which is irradiated onto an irradiation spot in the irradiation subject 4 in order to treat a focus, is determined. The determined desired number of accumulated particles is inputted to the computing processing unit 8, by use of, for example, an input terminal device. With reference to data, stored in the database 7, on the time dependency of the number of particles related to the amount of electric current that flows in the filament and the acceleration voltage to be applied to the electrodes of the RF acceleration mechanism, the computing processing unit 8 determines the amount of electric current that is made to flow in the filament and the acceleration voltage applied across the electrodes of the RF acceleration mechanism for realizing the desired number of accumulated particles. As described above, the desired accumulated number of particles may not necessarily be given from the outside; it may be allowed that the desired accumulated number of particles is preliminarily stored in the database 7.

The amount of electric current that is made to flow in the filament and the acceleration voltage applied to the electrodes of the RF acceleration mechanism, which have been determined by the computing processing unit 8, are transmitted to the accelerator 2; then, driving of the accelerator 2 is started. Until the operation of each of the ion source 11 and the RF acceleration mechanism 12 stabilizes and hence the particle distribution in a pulse of a particle beam becomes constant, the particle beam is blocked by a beam shutter provided at the output side, on the beam line 3, of the accelerator 2. At the time point when the particle distribution in a pulse of a particle beam becomes constant, the beam shutter is opened so that irradiation of the particle beam is started. This time point is referred to as an irradiation start time $t_{start}$.

Figure 3:
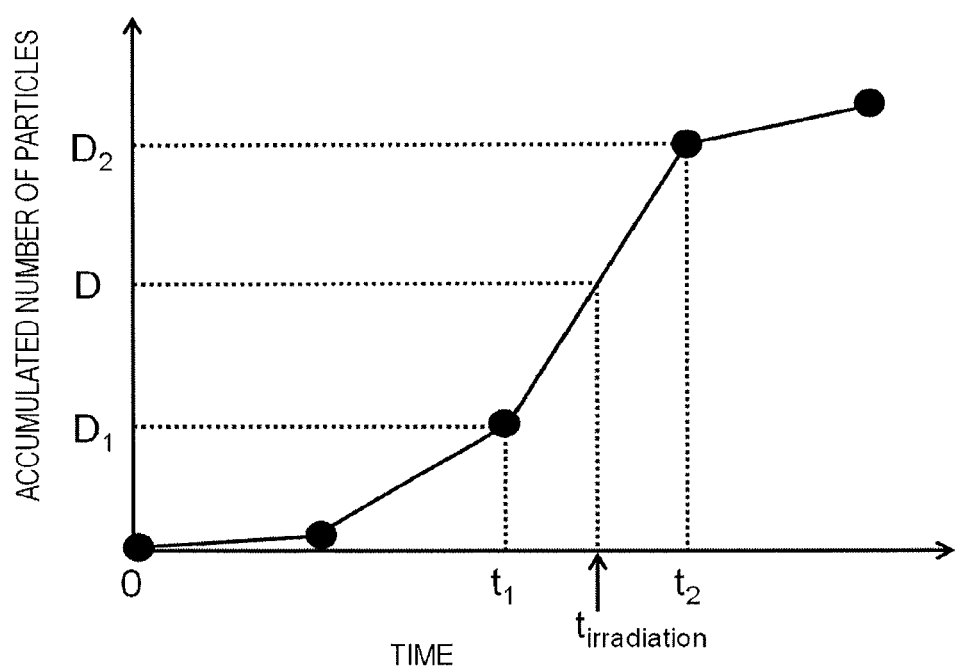
FIG. 3 is an explanatory graph for explaining the accumulated number of irradiation particles in one pulse according to Embodiment 1 of the present invention.

FIG. 3 is an explanatory graph for explaining the accumulated number of irradiation particles in one pulse according to Embodiment 1 of the present invention. The desired accumulated number of particles, which is determined through a treatment plan or the like, is referred to as "D". As represented in FIG. 3, data, stored in the database 7, on the time dependency of the number of particles in one pulse includes discrete values. It is assumed that the accumulated number of particles that is most close to but smaller than the desired accumulated number of particles D is referred to as an accumulated number of particles $D_1$, that the accumulated number of particles that is most close to but larger than the desired accumulated number of particles D is referred to as an accumulated number of particles $D_2$, and that the respective time points at which the accumulated number of particles reaches the accumulated number of particles $D_1$ and at which the accumulated number of particles reaches the accumulated number of particles $D_2$ are referred to as "$t_1$" and "$t_2$", respectively. In this situation, the time point $t_{irradiation}$ at which the accumulated number of particles reaches the desired accumulated number of particles D is calculated from the equation below.

$$t_{irradiation} = \{D \times (t_2 - t_1) - D_1 \times (t_2 - t_1)\}/(D_2 - D_1) + t_1$$

The acceleration frequency of the RF acceleration mechanism 12 in the accelerator and the timing at which the beam shutter is opened in order to irradiate a particle beam can be linked to each other; thus, the irradiation start time $t_{start}$ and the time point at which the pulse of the particle beam rises can be made to coincide with each other. In other words, it is made possible to make the irradiation start time $t_{start}$ coincide with 0 time in the abscissa of FIG. 3. The database 7 preliminarily stores a time difference $t_{rising}$ between the time point when the kicker electromagnet controller 6 receives the timing of the switching operation from the computing processing unit 8 and the time point when the switching operation by the kicker electromagnet 5 is completed.

The computing processing unit 8 transmits to the kicker electromagnet controller 6 a timing $t_{goal}$, of the switching operation by the kicker electromagnet 5, that is obtained by use of the $t_{start}$ at which the beam shutter is opened so that irradiation of a particle beam is started, the $t_{irradiation}$ calculated through the foregoing equation, and the $t_{rising}$ received from the database 7. In this situation, the timing $t_{goal}$ is calculated through the equation below.

$$t_{goal}+t_{start}+t_{irradiation}-t_{rising}$$

Figure 4:
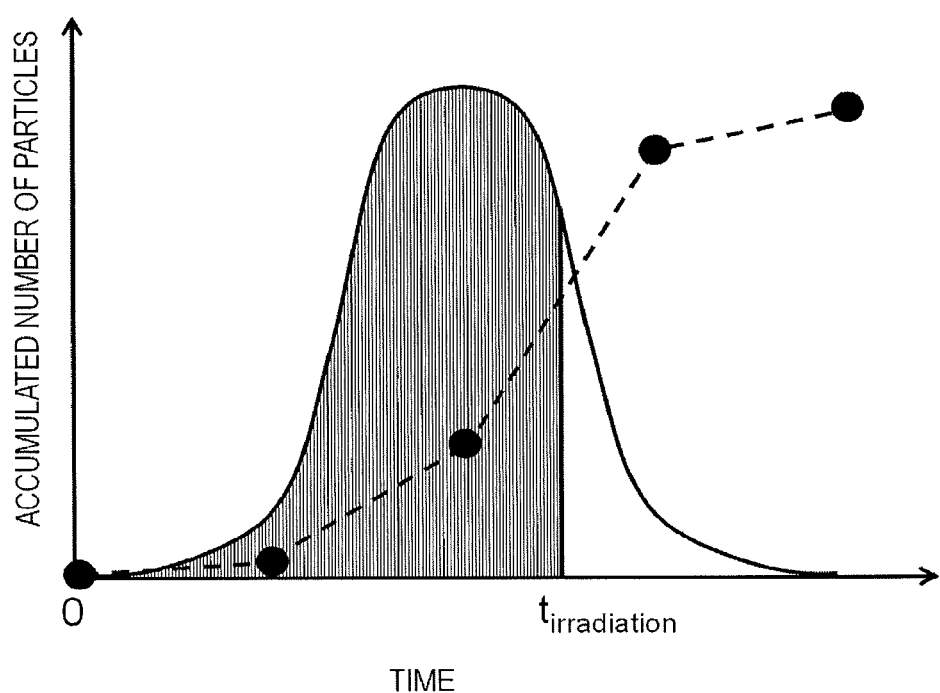
FIG. 4 is an explanatory graph for explaining the number of irradiation particles in one pulse according to Embodiment 1 of the present invention.

In actuality, at the timing of $t_{rising}+t_{goal}$ the kicker electromagnet 5 deflects a particle beam on the beam line 3 so as to divert the particle beam from the beam line 3. FIG. 4 is an explanatory graph for explaining the number of irradiation particles in one pulse in Embodiment 1 of the present invention. In Embodiment 1, as represented in FIG. 4, the particles in the portion (the hatching portion in FIG. 4), from the time point when pulse irradiation is started to the time $t_{irradiation}$, of an initial single pulse after irradiation of a particle beam is started are irradiated onto an irradiation spot in the irradiation subject 4, but the particles in the portion, after the time $t_{irradition}$, of the pulse are not irradiated.

In such a particle beam irradiation apparatus configured as described above, the time point at which the accumulated number of particles in one pulse becomes a desired accumulated number of particles is calculated by use of the time dependency of the number, of particles in one pulse of a particle beam, that corresponds to the driving condition for the accelerator, which is preliminarily stored in the database, and then the pulse is switched; therefore, the accumulated number of particles of a particle beam to be irradiated can be set to an arbitrary value.

To date, the driving condition for the accelerator has been set in such a way that the accumulated number of particles in one whole pulse becomes a desired accumulated number of particles; however, because the number of particles per pulse is set based on a table in which predetermined discrete beam control parameters (in the case of Embodiment 1, the amount of current in the filament and the acceleration voltage) and the number of particles per pulse are matched with each other, it is difficult to set the number of particles per pulse completely to an arbitrary value.

In Embodiment 1, the beam control parameters for the accelerator are not changed, and after the number of particles per pulse stabilized, the accumulated number of particles is set by use of a switching system; thus, the accumulated number of particles can be set to an arbitrary value.

Incidentally, to date, a method in which the accumulated number of particles is controlled by a blocking system provided in the path on the beam line 3 has existed. For example, a method in which data pieces on irradiated doses are counted by a dose monitor in a particle beam irradiation system and when the integration value thereof reaches a specified amount, a beam shutter is closed in order to stop the beam irradiation, a method in which a correlation between the beam control parameter and the number of particles per pulse is preliminarily obtained and at the timing when the number of particles per pulse reaches a predetermined accumulated number of particles, the particle beam is blocked, and the like have been known. However, in such a conventional method, the timing at which the blocking system blocks a particle beam is set between the pulses of a particle beam; therefore, it is not made possible to block the particle beam halfway through one pulse. This is because unlike Embodiment 1, such a conventional method does not utilize the time dependency of the number of particles in one pulse. Accordingly, in a conventional method in which the accumulated number of particles is controlled by a blocking system, the control of the number of particles can be performed only with a discrete value based on the number of particles per pulse. Moreover, it is not made possible to control the number of particles to be a value that is smaller than the number of particles in a single pulse.

In Embodiment 1, the time dependency of the number of particles in one pulse is utilized; therefore, the accumulated number of particles can be set to an arbitrary value; concurrently, it is also made possible to control the number of particles to be a value that is smaller than the number of particles in a single pulse.

In Embodiment 1, the driving condition for the accelerator has been explained with the amount of electric current that is made to flow in the filament and the acceleration voltage to be applied between the electrodes of the RF acceleration mechanism; however, other parameters may be utilized, depending on the method of the accelerator.

In Embodiment 1, as the switching system, a kicker electromagnet is utilized; however, instead of a kicker electromagnet, another mechanism such as an electric field shutter which switches a path of a particle beam by deflecting the particle beam with an electric field may be utilized.

In Embodiment 1, the particle number measurement monitor is installed so that before treatment utilizing the particle beam irradiation apparatus is started, the time dependency of the number of particles in one pulse of a particle beam is measured and is stored in the database 7.

Embodiment 2

The particle beam irradiation apparatus explained in Embodiment 1 is to irradiate a particle beam onto an irradiation spot, which is a single point. However, in the case where a particle beam irradiation apparatus is utilized in a particle beam therapy for treating a focus such as a tumor, a function of irradiating a particle beam onto a whole focus, which is an irradiation subject, is required. In Embodiment 2, a particle beam irradiation apparatus capable of performing scanning irradiation of a particle beam will be explained.

Figure 5:
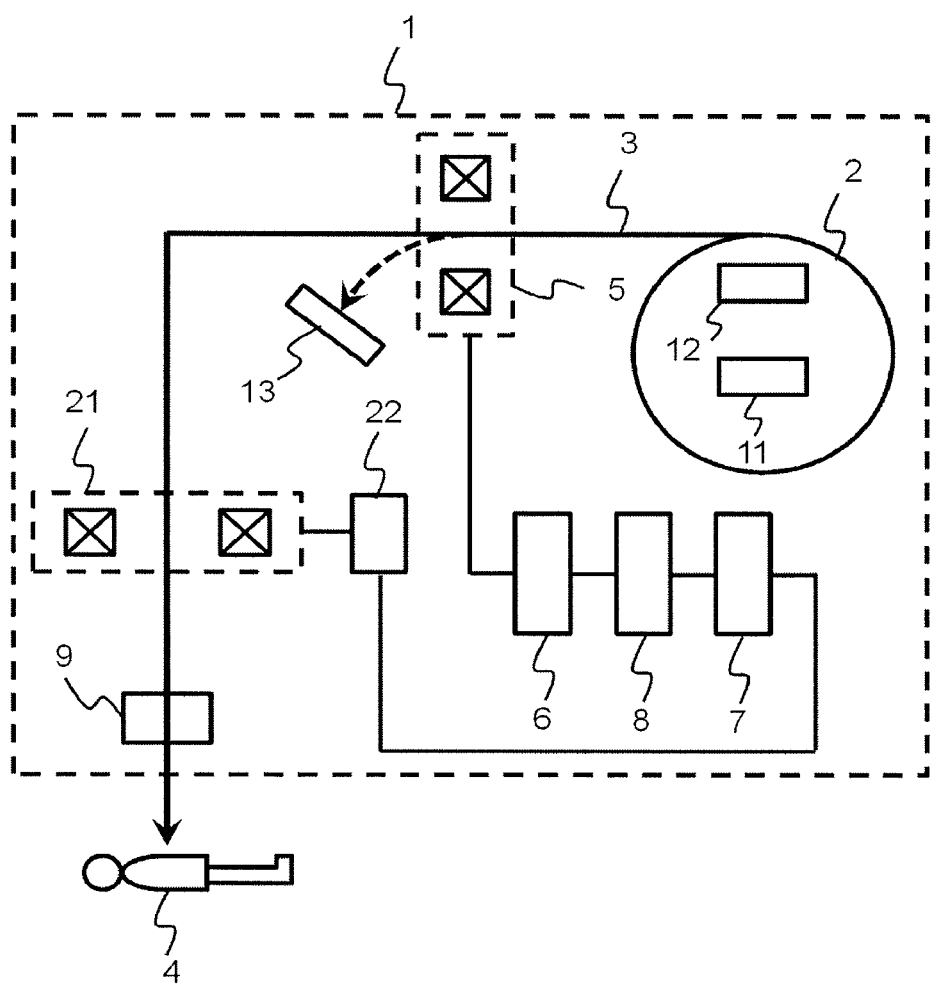
FIG. 5 is a schematic diagram of a particle beam irradiation apparatus representing Embodiment 2 of the present invention.

FIG. 5 is a schematic diagram of a particle beam irradiation apparatus according to Embodiment 2. As illustrated in FIG. 5, a particle beam irradiation apparatus 1 according to Embodiment 2 is configured in such a way that a scanning electromagnet 21, as a scanning system for providing a function of performing scanning irradiation, is added to the particle beam irradiation apparatus explained in Embodiment 1. The scanning electromagnet 21 is connected with a scanning electromagnet controller 22 for controlling the scanning electromagnet 21. The scanning electromagnet controller 22 can receive a signal from the database 7. The scanning electromagnet 21 is configured with two electromagnets with which the beam line 3 is flanked, and has an air-core structure; by changing the value of an electric current that is made to flow in the scanning electromagnet 21, the magnetic field is changed and hence it is made possible to scan a particle beam in a two-dimensional manner.

In order to irradiate a particle beam onto a whole focus, which is an irradiation subject, it is required to control the particle beam in a three-dimensional manner. A particle beam has a nature that after traveling a certain distance through a living body, it provides drastically high energy to its surroundings and then disappears there. The distance in which a particle beam travels through a living body is determined by the energy of the particle beam. Accordingly, when it is assumed that the direction in which a particle beam travels through a living body is the z-axis direction and, for example, that the energy of the particle beam is constant, an irradiation position of the z-axis-direction can be controlled by changing energy with use of a thick plate, which is referred to as a range shifter. By setting the direction, in which the scanning electromagnet scans a particle beam, on the xy plane, and in combination with the range shifter, the particle beam can be controlled in a three-dimensional manner (in the x-, y-, and z-axis directions).

With regard to a focus, which is an irradiation subject, the three-dimensional position of an irradiation spot onto which a particle beam is to be irradiated and a desired accumulated number of particles at the irradiation spot are determined through a treatment plan. Furthermore, through the treatment plan, the order of irradiation spots is determined based on the positions of the irradiation spots and the respective desired accumulated numbers of particles. These data pieces are inputted to the database 7.

In the database 7, the amount of electric current that flows in the filament of the ion source 11 and the acceleration voltage to be applied between the electrodes of the RF acceleration mechanism 12 are utilized as parameters, and the time dependency of the number, of particles in one pulse of a particle beam, that corresponds to the parameters, is stored. Moreover, in the database 7, the (x- and y-axis) positions of each irradiation spot, the desired accumulated number of particles at the depth-direction (z-axis) position, and the order of the irradiation spots are stored.

In the order of the irradiation spots, the database 7 transmits the (x- and y-axis) positions of the initial first irradiation spot to the scanning electromagnet controller 22; concurrently, the database 7 also transmits to the computing processing unit 8 the time dependency of the number of particles and the desired accumulated number of particles, at the irradiation spot, related to the amount of electric current that flows in the filament of the ion source 11 and the acceleration voltage to be applied to the electrodes of the RF acceleration mechanism 12.

Based on the data received from the database 7, the computing processing unit 8 calculates the irradiation time of a particle beam, which corresponds to the desired accumulated number of particles, so as to compute the timing of the switching operation, at the first irradiation spot, by the kicker electromagnet 5. The kicker electromagnet controller 6 controls the switching operation performed by the kicker electromagnet 5 at the timing of the switching operation by the kicker electromagnet 5, which has been computed by the computing processing unit 8.

Then, in a procedure similar to that in Embodiment 1, a particle beam is irradiated onto the first irradiation spot. When the irradiation onto the first irradiation spot has been completed, the irradiation position is moved to the second irradiation spot, while switching is performed by the kicker electromagnet 5. After the irradiation position has been moved to the second irradiation spot, the switching by the kicker electromagnet 5 is cancelled; then, in the same procedure, a particle beam is also irradiated onto each of the irradiation spot after and including the second irradiation spot. After the irradiation of a particle beam onto the first irradiation spot has been completed, the database 7 sequentially transmits data on the irradiation spot to the scanning electromagnet controller 22 and the computing processing unit 8, so that a particle beam including particles corresponding to the desired accumulated number of particles is recurrently irradiated onto each of the corresponding irradiation spots.

In such a particle beam irradiation apparatus configured as described above, the time point at which the accumulated number of particles in one pulse becomes a desired accumulated number of particles is calculated by use of the time dependency of the number, of particles in one pulse of a particle beam, that corresponds to the driving condition for the accelerator, which is preliminarily stored in the database, and then the pulse is switched; therefore, the accumulated number of particles of a particle beam to be irradiated can be set to an arbitrary value.

Moreover, the particle beam irradiation apparatus is provided with a scanning system having a function of performing scanning irradiation; therefore, the accumulated number of particles of a particle beam to be irradiated onto each of the irradiation spots in a focus, which is an irradiation subject, can be set to an arbitrary individual value.

Embodiment 3

In the case where a particle beam irradiation apparatus is utilized in a particle beam therapy for treating a focus such as a tumor, excessive irradiation should be prevented. In Embodiment 3, a particle beam irradiation apparatus provided with a safety device for preventing excessive irradiation will be explained.

Figure 6:
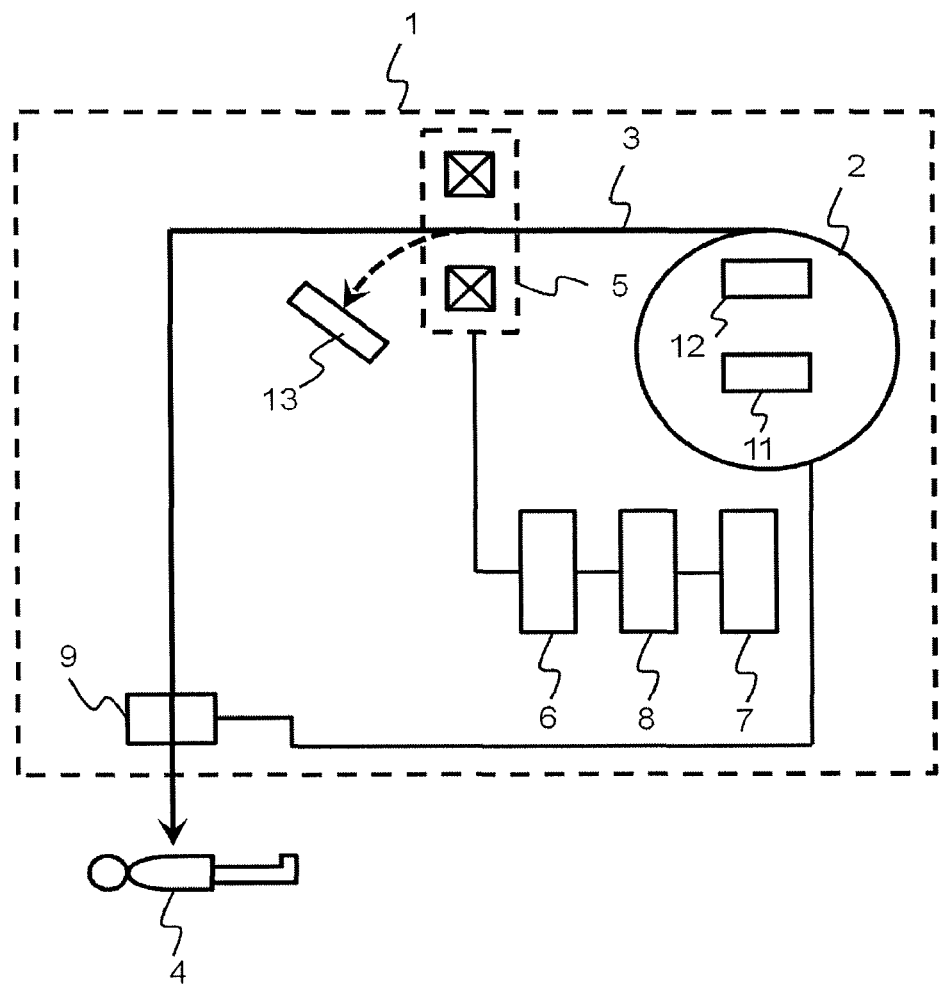
FIG. 6 is a schematic diagram of a particle beam irradiation apparatus representing Embodiment 3 of the present invention.

FIG. 6 is a schematic diagram of a particle beam irradiation apparatus according to Embodiment 3. As illustrated in FIG. 6, in a particle beam irradiation apparatus 1 according to Embodiment 3, the accelerator 2 is connected with the particle number measurement monitor 9 provided between the kicker electromagnet 5, as a switching system, and the irradiation subject 4.

In Embodiment 3, the operation of the particle beam irradiation apparatus 1 at a time when a normal treatment is performed is the same as that of the particle beam irradiation apparatus 1 according to Embodiment 1. However, due to noise or the like generated in a signal transmission path, for example, between the database 7 and the computing processing unit 8 or between the computing processing unit 8 and the kicker electromagnet controller 6, a control signal may erroneously be transmitted. As a result, the accumulated number of particles to be irradiated may exceed a desired accumulated number of particles (excessive irradiation).

In Embodiment 3, the particle number measurement monitor 9 is provided between the kicker electromagnet 5 and the irradiation subject 4; the number of particles irradiated onto the practical irradiation subject 4 is preliminarily counted by the particle number measurement monitor 9; in the case where the number of particles irradiated onto the practical irradiation subject 4 exceeds the desired accumulated number of particles, the beam shutter of the accelerator 2 is closed so that irradiation of the particle beam is stopped.

In such a particle beam irradiation apparatus configured as described above, as is the case with Embodiment 1, the time point at which the accumulated number of particles in one pulse becomes a desired accumulated number of particles is calculated by use of the time dependency of the number, of particles in one pulse of a particle beam, that corresponds to the driving condition for the accelerator, which is preliminarily stored in the database, and then the pulse is switched; therefore, the accumulated number of particles of a particle beam to be irradiated can be set to an arbitrary value. Moreover, because the particle beam irradiation apparatus is provided with the particle number measurement monitor 9, it is made possible to suppress excessive irradiation onto an irradiation subject at a minimum level even when the control signal may erroneously be transmitted and hence excessive irradiation may be caused.

Embodiment 4

In the case where a particle beam irradiation apparatus is utilized in a particle beam therapy for treating a focus that is shifted by respiration, a particle beam may be irradiated onto a site other than the focus, depending on the shifting amount thereof. In Embodiment 4, a particle beam irradiation apparatus, provided with a function in which in order to prevent irradiation onto a site other than a focus, beam irradiation is interrupted when respiration causes a focus to shift by more than a specified amount, will be explained.

Figure 7:
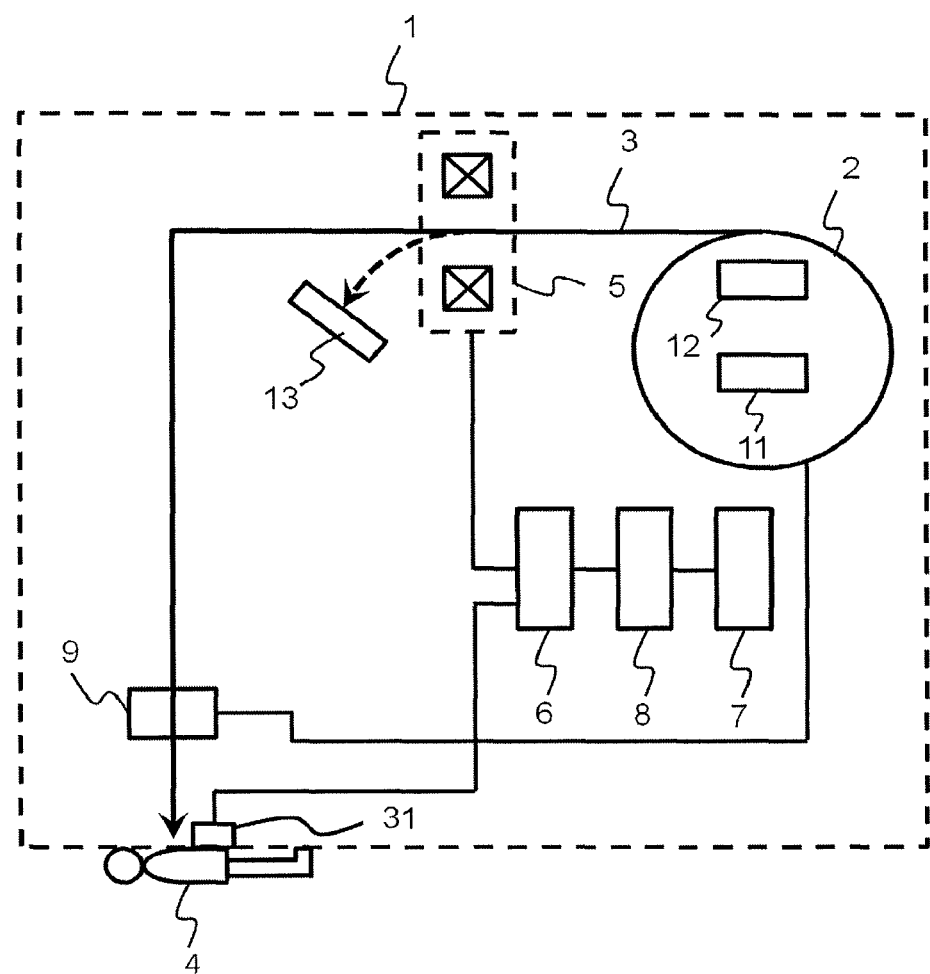
FIG. 7 is a schematic diagram of a particle beam irradiation apparatus representing Embodiment 4 of the present invention.

FIG. 7 is a schematic diagram of a particle beam irradiation apparatus according to Embodiment 4. As illustrated in FIG. 7, a particle beam irradiation apparatus 1 according to Embodiment 4 is configured in such a way that a respiration monitor 31 that functions as a shift sensor for measuring the shifting amount of a focus is further added to the particle beam irradiation apparatus illustrated in FIG. 6 of Embodiment 3. The respiration monitor 31 is to be mounted on the surface of a patient body, which is the irradiation subject 4; it is mounted on the surface of a body that shifts, when a focus shifts due to respiration, in proportion to the shifting amount of the focus. The output of the respiration monitor 31 is connected with the kicker electromagnet controller 6. The respiration monitor 31 is mounted at a position where it does not obstruct irradiation of a particle beam.

Next, practical use of the respiration monitor 31 in Embodiment 4 will be explained. At first, by use of the respiration monitor 31, the relationship between a reference position on the surface of a patient body and the shifting amount of the surface of the patient body from the reference position is preliminarily obtained. Next, the relationship between the shifting amount of the surface of the patient body and the shifting amount of a focus, which is a treatment subject, is preliminarily obtained by use of a method such as an MRI (Magnetic Resonance Imaging) scan. The shifting amount, in the respiration monitor 31, of the body surface from the reference position, with respect to the shifting amount of the focus at a time when a particle beam may be irradiated onto a site other than the focus, is set as a threshold value.

When after the particle beam therapy has been started, the shifting amount of the body surface, measured by the respiration monitor 31, exceeds the threshold value, the respiration monitor 31 transmits a signal to the kicker electromagnet controller 6 so as to immediately start the switching operation by the kicker electromagnet 5, thereby diverting the particle beam from the beam line 3. When the shifting amount is smaller than the threshold value, the respiration monitor 31 transmits a signal to the kicker electromagnet controller 6 so as to immediately stop the switching operation by the kicker electromagnet 5, thereby transporting the particle beam onto the beam line 3. The system that, as described above, detects the shift of a focus, caused by respiration, by use of a respiration monitor, and controls irradiation of a particle beam is defined as a respiration synchronization system.

In the case where the respiration synchronization system interrupts irradiation halfway through the one-pulse period of a particle beam, the accumulated number of particles for the irradiation subject does not reach the desired accumulated number of particles. In order to make the accumulated number of particles for the focus to be the desired accumulated number of particles, the following method may preferably be utilized.

When the respiration synchronization system interrupts irradiation, the accumulated number of particles, recorded in the particle number measurement monitor 9, is transmitted to the computing processing unit 8. The computing processing unit 8 adopts, as a new desired accumulated number of particles, the accumulated number of particles, which is obtained by subtracting the transmitted accumulated number of particles from the desired accumulated number of particles; based on the time dependency of the number of particles, stored in the database 7, irradiation is performed in a manner that is the same as that in Embodiment 1.

In a particle beam irradiation apparatus configured as described above, use of the respiration synchronization system makes it possible to prevent irradiation onto a site other than a focus, even when respiration shifts the focus. Furthermore, even in the case where the respiration synchronization system interrupts irradiation of a particle beam halfway through the one-pulse period, the interruption timing for the next pulse can be determined based on the accumulated number of particles at the time immediately before the interruption; therefore, even when the respiration synchronization system is utilized, the accumulated number of particles of a particle beam to be irradiated can be set to an arbitrary value.

In Embodiment 4, an example in which a respiration monitor is utilized as the shift sensor has been described; however, as the shift sensor for measuring the shifting amount of a focus, another method may be utilized. For example, the shift sensor may be configured in such a way that metal, which is a marker, is injected into a focus or the vicinity of the focus and by use of an MRI or the like, the shifting amount of the metal is measured in real time.

In addition, it may be allowed that the configuration of the particle beam irradiation apparatus explained in Embodiment 4 and the configuration of the particle beam irradiation apparatus explained in Embodiment 2 or 3 are combined with each other.

Various modifications and alterations of this invention will be apparent to those skilled in the art without departing from the scope and spirit of this invention, and it should be understood that this is not limited to the illustrative embodiments set forth herein.

What is claimed is:
1. A particle beam irradiation apparatus comprising:
an accelerator that extracts a particle beam of a pulse shape;
a switching system that switches the particle beam extracted from the accelerator to prevent irradiation of an irradiation subject with the particle beam;
a database memory that pre-stores a database in which time dependency of the number of particles in one pulse of the particle beam is stored in association with a driving condition for the accelerator; and
a processor, including a computer and a memory, that
calculates a switching timing for the switching system based on a desired accumulated number of particles to be irradiated onto the irradiation subject and the time dependency of the number of particles in one pulse of the particle beam that is stored in the database memory, and
controls the switching system based on the switching timing calculated.

2. The particle beam irradiation apparatus according to claim 1, further comprising a scanning system that scans the particle beam in a two-dimensional manner onto the irradiation subject.

3. The particle beam irradiation apparatus according to claim 1, wherein the switching system is a kicker electromagnet.

4. The particle beam irradiation apparatus according to claim 3, further comprising a beam damper that absorbs and extinguishes a particle beam deflected by the kicker electromagnet in a direction other than a direction to the irradiation subject.

5. The particle beam irradiation apparatus according to claim 1, further comprising a particle number measurement monitor that measures the number of particles in a particle beam to be irradiated onto the irradiation subject.

6. The particle beam irradiation apparatus according to claim 5, further comprising a shift sensor that detects a shifting amount of an irradiation subject, wherein when the shifting amount of the irradiation subject detected by the shift sensor exceeds a threshold value, the switching system switches the particle beam to prevent further irradiation of the irradiation subject.

7. The particle beam irradiation apparatus according to claim 6, wherein when a shifting amount of an irradiation subject detected by the shift sensor exceeds the threshold value, the number of particles in the particle beam measured by the particle number measurement monitor is transmitted to the processor, and the processor calculates a new desired accumulated number of particles by subtracting the number of particles transmitted from the particle number measurement monitor from the desired accumulated number of particles.

* * * * *